US00PP23150P2

(12) United States Plant Patent
Klemm et al.

(10) Patent No.: US PP23,150 P2
(45) Date of Patent: Oct. 30, 2012

(54) CARNATION PLANT NAMED 'KLEDG11143'

(50) Latin Name: *Dianthus caryophyllus*
Varietal Denomination: KLEDG11143

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 13/135,748

(22) Filed: Jul. 14, 2011

(51) Int. Cl.
*A01H 5/00* (2006.01)

(52) U.S. Cl. ..... Plt./273

(58) Field of Classification Search ..... Plt./273
See application file for complete search history.

*Primary Examiner* — Annette Para

(74) *Attorney, Agent, or Firm* — Jondle & Associates, P.C.

(57) ABSTRACT

A new variety of Carnation named 'KLEDG11143' particularly characterized by its compact growth, early flowering, and dark purple flowers with light borders, is disclosed.

1 Drawing Sheet

Genus and species: *Dianthus caryophyllus*.
Variety denomination: 'KLEDG11143'.

BACKGROUND OF THE NEW PLANT

The present invention comprises a new and distinct variety of carnation, botanically known as *Dianthus caryophyllus*, and hereinafter referred to by the variety name 'KLEDG11143'. The new variety is the result of a cross conducted in July 2006 in Stuttgart, Germany between the proprietary female parent carnation plant, '*Dianthus×allwoodii*' (unpatented) and the proprietary male parent, 'DCP 06 030' (unpatented). A single plant selection was subsequently chosen for further evaluation and for asexual propagation. The new variety was first propagated via vegetative cuttings in June 2007 in Stuttgart, Germany and has been asexually reproduced repeatedly by vegetative cuttings in Stuttgart, Germany for approximately six to seven generations. 'KLEDG11143' has been found to retain its distinctive characteristics through successive asexual propagations via vegetative cuttings.

'KLEDG11143' has not been made publicly available or sold more than one year prior to the filing date of this application.

SUMMARY OF THE INVENTION

The following are the most outstanding and distinguishing characteristics of this new variety when grown under normal horticultural practices in a greenhouse in Stuttgart, Germany.

1. Compact growth;
2. Early flowering; and
3. Dark purple flowers with light borders

DESCRIPTION OF THE PHOTOGRAPH

This new carnation plant is illustrated by the accompanying photograph which shows the flowers and foliage of the plant. The colors shown are as true as can be reasonably obtained by conventional photographic procedures. The photograph was taken in April 2010 of a 5-month-old plant grown from rooted cuttings in a 10 centimeter pot in a glass-covered greenhouse in Stuttgart, Germany under conditions which approximate those generally used in horticultural practice.

DESCRIPTION OF THE NEW VARIETY

The following detailed descriptions set forth the distinctive characteristics of 'KLEDG11143'. The data which define these characteristics were collected from asexual reproductions carried out in Stuttgart, Germany. The plant history was taken in Spring 2010 on 5-month-old plants in 10 centimeter pots that were pinched once at week 45 and grown in a glass-covered greenhouse. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family*.—Caryophyllaceae.
- *Genus and species*.—*Dianthus caryophyllus*.
- *Common name*.—Carnation.

Parentage:
- *Female parent*.—The proprietary carnation '*Dianthus×allwoodii*' (unpatented).
- *Male parent*.—The proprietary carnation 'DCP 06 030' (unpatented).

Plant:
- *Form*.—Potted plant.
- *Habit*.—Upright, round.
- *Height (from top of soil)*.—12.0 cm to 15.0 cm.
- *Width (spread)*.—12.0 cm to 15.0 cm.
- *Life cycle*.—Perennial.
- *Flowering habit*.—Continuous.
- *Time to produce a finished flowering plant*.—4 months.
- *Propagation type*.—Vegetative cuttings.
- *Time to initiate roots*.—20 days.
- *Root description*.—Fine; RHS NN155C (White).
- *Temperature tolerances*.—+30° C. to −15° C.

Branches:
- *Strength*.—Medium.
- *Quantity per plant*.—7 to 9.
- *Color*.—RHS 126B.
- *Length*.—4.0 cm to 8.0 cm.
- *Diameter*.—0.4 cm to 0.6 cm.

*Internode length.*—0.5 cm.
*Texture.*—Smooth.

Leaves:
*Arrangement.*—Opposite.
*Shape.*—Lanceolate.
*Apex.*—Acute.
*Base.*—Obtuse.
*Margin.*—Entire.
*Color.*—Immature leaf (both upper and lower surfaces): RHS 126C. Mature leaf (both upper and lower surfaces): RHS 126C.
*Length.*—5.0 cm to 6.0 cm.
*Width.*—0.4 cm to 0.5 cm.
*Texture.*—Smooth.
*Venation pattern.*—Pinnate.
*Venation color* (*both upper and lower surfaces*).—RHS 126C.
*Petioles.*—Absent.

Flowers:
*Blooming habit.*—Small sprays.
*Flower type.*—Double.
*Flowering season.*—Early Spring to late Fall.
*Width.*—3.0 cm.
*Depth.*—2.0 cm.
*Shape.*—Round.
*Fragrance.*—Present.
*Number of flowers per plant.*—3 to 4.

Flower buds:
*Color.*—RHS N77B.
*Shape.*—Elliptic.
*Length.*—0.6 cm to 1.8 cm.
*Diameter.*—0.5 cm to 0.8 cm.

Petals:
*Arrangement.*—Arranged in several whorls.
*Quantity* (*per flower*).—Greater than 20.
*Shape.*—Spoon-shaped.
*Apex.*—Obtuse.
*Margin.*—Serrate.
*Base.*—Acute.
*Length.*—1.5 cm.
*Width.*—1.3 cm.
*Color.*—When opening: Upper surface: RHS N79B and RHS 63B (at eye). Lower surface: RHS 71B. When fully opened: Upper surface: RHS N79C and RHS 63B (at eye). Lower surface: RHS 71B.
*Texture* (*both surfaces*).—Smooth.

Sepals:
*Calyx.*—Form: Cylinder vase. Length: 1.8 cm. Width: 0.8 cm to 1.0 cm.
*Arrangement.*—Fused.
*Quantity* (*per flower*).—4 to 5.
*Shape.*—Elliptic.
*Apex.*—Acute.
*Base.*—Obtuse.
*Margin.*—Smooth.
*Length.*—0.6 cm.
*Width.*—0.6 cm.
*Color.*—Upper surface: RHS N77B and RHS 137B. Lower surface: RHS N77B and RHS 137C.
*Texture* (*both surfaces*).—Smooth.

Peduncle:
*Length.*—5.0 cm to 8.0 cm.
*Diameter.*—0.2 cm to 0.3 cm.
*Texture.*—Smooth.
*Color.*—RHS 126C.

Reproductive organs:
*Pistils.*—Quantity: 1. Stigma color: RHS 63A through RHS 63D and RHS 69D. Ovary color: RHS 144D.
*Stamens.*—Quantity: Moderate. Filament: Length: 0.5 cm to 1.2 cm. Color: RHS 69D, and RHS 63A through RHS 63D. Anther color: RHS 63A. Pollen: Amount: Moderate. Color: RHS 69C.

Fruit and seed set: None observed.

Disease and insect resistance: No particular resistance or susceptibility to common carnation diseases or insect pests has been observed.

COMPARISON WITH PARENTAL VARIETIES

'KLEDG11143' differs from the female parent, the proprietary carnation plant '*Dianthus×allwoodii*' (unpatented), in that 'KLEDG11143' has double, dark purple flowers, while '*Dianthus×allwoodii*' has semi-double, light pink flowers.

'KLEDG11143' differs from the male parent, the proprietary carnation plant 'DCP 06 030' (unpatented), in that 'KLEDG11143' has dark purple flowers, compact growth, and small leaves, while 'DCP 06 030' has dark purple flowers, stronger growth, and wide leaves.

We claim:

1. A new and distinct variety of Carnation plant named 'KLEDG11143' as shown and described herein.

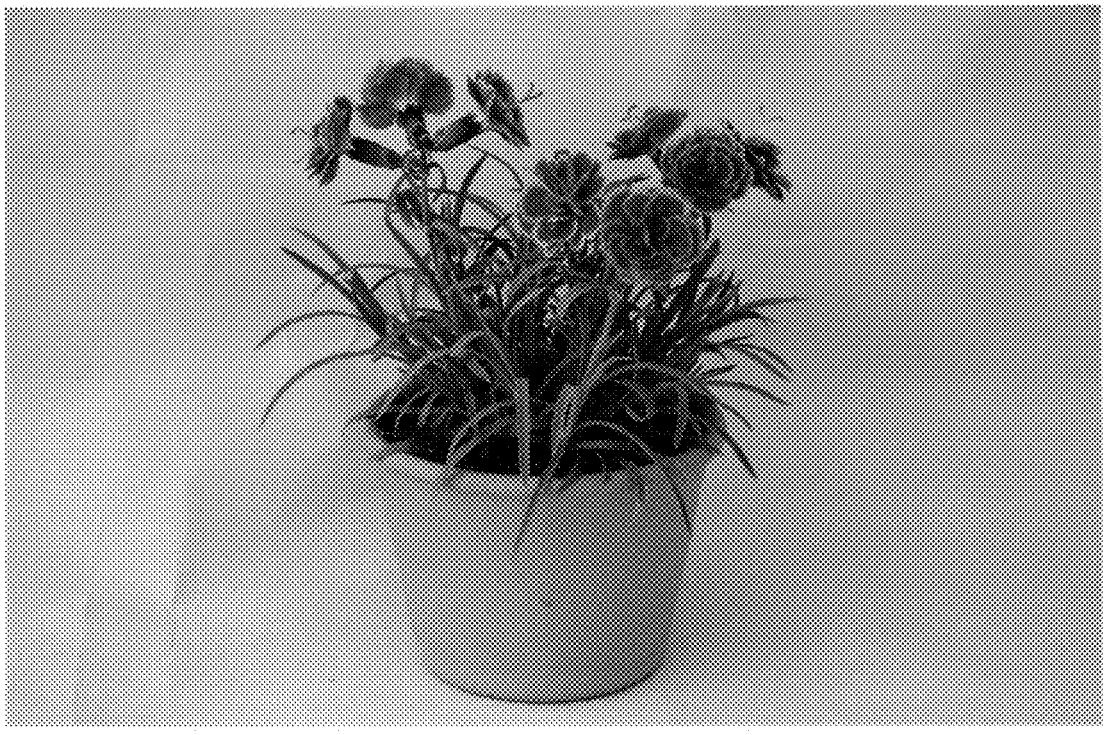

* * * * *